United States Patent [19]

Traber et al.

[11] Patent Number: 5,155,128
[45] Date of Patent: Oct. 13, 1992

[54] MEDICAMENTS FOR THE TREATMENT OF CEREBRAL APOPLEXY

[75] Inventors: Jörg Traber, Lohmar; Gerhard-Wilhelm Bielenberg, Amoeneburg, both of Fed. Rep. of Germany

[73] Assignee: Troponwerke GmbH & Co., Cologne, Fed. Rep. of Germany

[21] Appl. No.: 714,470

[22] Filed: Jun. 13, 1991

Related U.S. Application Data

[62] Division of Ser. No. 579,414, Sep. 10, 1990, Pat. No. 5,070,102, which is a division of Ser. No. 407,161, Sep. 14, 1989, Pat. No. 4,988,700.

[30] Foreign Application Priority Data

Sep. 20, 1988 [DE] Fed. Rep. of Germany ....... 3831888

[51] Int. Cl.$^5$ ................. A61K 31/131; A61K 31/335
[52] U.S. Cl. ..................................... 514/452; 514/646
[58] Field of Search ................................ 514/452, 646

[56] References Cited

U.S. PATENT DOCUMENTS 5,049,588  9/1991  Nicholson et al. ................. 514/646

OTHER PUBLICATIONS

Journal of Neurology, Neurosurgery, and Psychiatry, Feb. 1981, vol. 44, No. 2.
Intensive Care Medicine, vol. 9, 1983, pp. 123–126.
Brain Research, vol. 435, No. 1–2, 1987, pp. 305–309.
Neurology, vol. 35, No. 4, Apr. 1985, pp. 584–587.
Chem. Abst.—112(1990) 211004y refer to 1988 Article.

*Primary Examiner*—S. J. Friedman
*Attorney, Agent, or Firm*—Sprung Horn Kramer & Woods

[57] ABSTRACT

A method of treating cerebral apoplexy in a patient in need thereof which comprises administering to said patient an amount effective therefor of a serotonin agonist which has a binding strength of less than 10,000 nmol/l on binding to $5HT_{1A}$ receptors.

4 Claims, No Drawings

MEDICAMENTS FOR THE TREATMENT OF CEREBRAL APOPLEXY

This is a division, of application Ser. No. 579,414, filed Sep. 10, 1990, now allowed as U.S. Pat. No. 5,070,102, which is a division of application Ser. No. 407,161, filed Sep. 14, 1989, now U.S. Pat. No. 4,988,700.

The invention relates to the use of active compounds which act as serotonin agonists and have a binding strength of less than 10,000 nmol/l on binding to $5HT_{1A}$ receptors for the preparation of medicaments for the treatment of cerebral apoplexy.

Cerebral apoplexy (stroke, cerebrovascular accident) is a consequence of a sudden disturbance of blood flow in a region of the human brain with subsequent functional deficits and with corresponding neurological and/or psychological symptoms. Cerebral apoplexy may be caused by brain haemorrhages (for example following a vessel rupture in cases of hypertension, arteriosclerosis and apoplectic aneurysm) and ischaemias (for example due to a hypotensive crisis or embolism). The functional deficits in the brain result in degeneration and/or death of brain cells (Journal of Cerebral Blood Flow and Metabolism 1:155 to 185 (1981)).

The use of active compounds which act as serotonin agonists and have a binding strength of less than 10,000 nmol/l on binding to $5HT_{1A}$ receptors for the preparation of medicaments for the treatment of cerebral apoplexy has been found.

The active compounds according to the invention surprisingly bring about, both with prophylactic treatment and with treatment (therapeutic) taking place after the cerebral apoplexy, a great reduction in the degeneration and/or the death of brain cells, and they prevent or reduce the functional deficits in the brain.

Active compounds which act as serotonin agonists can be identified by determining the inhibition of the forskolin-stimulated adenylate cyclase activity ($EC_{50}$ value) by the relevant active compound (J. Pharmacol Exp. Ther. 238, 248–253 (1986)). $5HT_{1A}$ ligands which act as agonists or partial agonists inhibit forskolin-stimulated adenylate cyclase. Active compounds which reduce the enzyme activity act as serotonin agonists or partial serotonin agonists. The said adenylate cyclase inhibition test can be carried out as follows, for example:

Rat hippocampus membranes are incubated under suitable conditions with $\alpha$-$^{32}$P-ATP and forskolin in the absence and presence of compounds according to the invention. After the reaction has been stopped, the radioactively labelled cyclic AMP is isolated and quantitatively determined. The enzyme activity is calculated from this.

The binding strength (inhibition constant or $K_i$ value) is a measure of the interactions between an active compound and the $5HT_{1A}$ serotonin receptors (Molecular Pharmacology 16, 687–699 (1979); J. Neurochem. 36, 220–226, 1981).

The binding strength can be determined as follows, for example:

Calf hippocampus membranes are incubated with $^3$H-serotonin in the presence and absence of substances according to the invention. The reaction is stopped by filtration, and the radioactivity remaining on the filters is measured. $IC_{50}$ values and inhibition constants $K_i$ are calculated from the resulting displacement plots.

Preferred active compounds which act as serotonin agonists and have a binding strength of less than 10,000 nmol/l on binding to $5HT_{1A}$ receptors are described, for example, in SCRIP's Serotonin Report, PJB Publications (1988) and by J. Fozard, Trends in Pharmacological Sciences 8, 501 (1987).

These include, for example, compounds from the following classes of substances aryl-and hetaryl-piperazines (disclosed inter alia also in DE-A 220,873; DE-A 3,321,969; EP-A 82,402; DE-A 3,529,872; DE-A 3,248,160), aminotetrahydrobenzindoles (DE-A 3,346,573; EP-A 153,083; EP-A 162,695), indolamines (inter alia Fozard, Trends in Pharmacological Sciences 8, 501 (1987); Scrip's Serotonin Report, PJB Publications (1988); EP-A 236,930, DE-A 3,131,728; DE-A 2,940,687; DE-A 3,320,521), aminoalkyl-benzadioxanes (inter alia Fozard, Trends in Pharmacological Sciences 8, 501 (1987); Scrip's Serotonin Report, PJB Publications (1988); EP-A 236,930; EP-A 170,213), amino-tetralins (inter alia Fozard, Trends in Pharmacological Sciences 8, 501 (1987); Scrip's Serotonin Report, PJB Publications (1988); EP-A 41,488; EP-A 236,930), amino-chromans and -thiopyrans (for example EP-A 222,996), indolyl-alkyl-piperidines (DE-A 3,430,284), tetrahydropyridines (for example from Fozard, Trends in Pharmacological Sciences 8, 501 (1987); Scrip's Serotonin Report, PJB Publications (1988); EP-A 3,199).

Particularly preferred from the group of aryl- and hetaryl-piperazines are the 2-pyrimidinyl-1-piperazine derivatives of the formula I

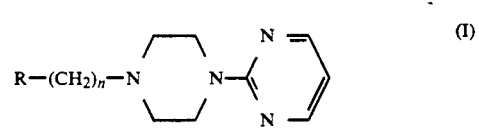

and the aryl-1-piperazine derivatives of the formula II

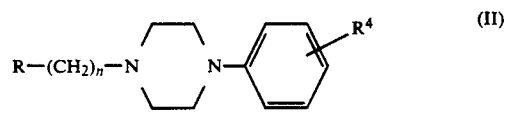

in which
n represents one of the numbers 2, 3, 4, 5 or 6,
R represents one of the radicals

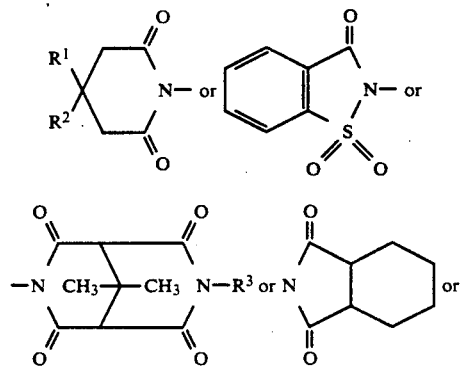

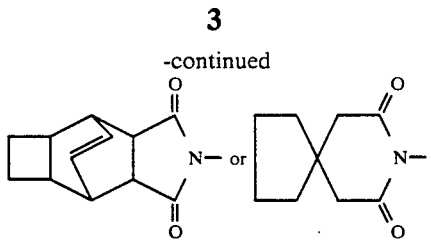

in which

R¹ and R² are identical or different and denote hydrogen or lower alkyl ($C_1$ to about $C_6$), R³ represents alkyl ($C_1$ to about $C_6$) or alkenyl, and R⁴ represents hydrogen, alkoxy ($C_1$ to $C_6$) or halogen, and/or the salts thereof.

Others which may also be mentioned are (+)-N-[2-[4-[2,3-dihydro-2-(hydroxymethyl)-1,4-benzodioxin-5-yl]-1-piperazinyl]ethyl]-4-fluorobenzamide hydrochloride (INN: flesinoxan hydrochloride) and 6-[[3-[4-[o-methoxyphenyl]-1-piperazinyl]propyl]amino]-1,3-dimethyluracil [INN: urapidil].

The following active compounds may be mentioned by way of example: 8-[4-N-[4-(2-pyrimidinyl)-1-piperazinyl]-butyl]-8-azaspiro[4.5]-decane-7,9-dione hydrochloride (INN: buspirone), 4,4-dimethyl-1-[4-[4-(2-pyrimidinyl)-1-piperazinyl]-butyl]-2,6-piperidinedione hydrochloride (INN: gepirone), 2-(4-(4-(2-pyrimidinyl)-1-piperazinyl)-butyl)-1,2-benzoisothiazol-3(2H)-one 1,1-dioxide hydrochloride (INN: ipsapirone), 3a,4,4a,6a,7-,7a-hexahydro-2-[4-[4-(2-pyrimidinyl)-1-piperazinyl]-butyl]-4,7-etheno-1H-cyclobutano[f]isoindole-1,3(2H)-dione dihydrochloride sesquihydrate (WY-47,846), N-[4-[4-(2-pyrimidinyl)-1-piperazinyl]butyl]-bicyclo[2.2.1-]heptane-2,3-di-exo-carboximide (SM 3997), 2-(4-(4-(2-pyrimidinyl)-1-piperazinyl-propyl)-1,2-benzoisothiazol-3-(2H)-one 1,1-dioxide hydrochloride, 3-butyl-9,9-dimethyl-7-[4-[4-[2-methoxyphenyl]-1-piperazinyl]-butyl]-3,7-diazabicyclo[3,2,1]nonane-2,4,6,8-tetraone (KC 9172).

Ipsapirone is particularly preferred.

The piperazine derivatives are known per se (DE-A-3,321,969; Fozard, Trends in Pharmacological Sciences 8, 501 (1987); Scrip Report, PJB Publications (1988); EP-A 82,402; EP-A 220,873; DE-A 3,529,872; DE-A 3,248,160) and can be prepared, for example, by reacting an appropriate benzothiazole with (piperazinyl)-pyrimidines.

Particularly preferred from the group of tetrahydrobenzindoles are the 1,3,4,5-tetrahydrobenz[c,d]indoles of the formula

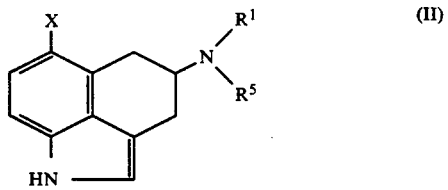

in which

X represents H, OCH₃, OH, SCH₃, halogen, CN or CONH₂,

R¹ has the abovementioned meaning, and

R⁵ has the meaning indicated above for R¹ or represents—Y-Z, where

Y represents a straight-chain saturated or unsaturated alkylene chain having up to 6 carbon atoms, and Z represents an amino, alkoxy ($C_1$ to $C_6$), sulphonamido or carboxamido group or a heterocycle, and/or the salts thereof.

The following active compounds may be mentioned by way of example:

4-(N,N-dipropylamino)-6-methoxy-1,3,4,5-tetrahydrobenz-[c,d]indole, 4-[4-(N-1,2-benzisothiazol-3(2H)-one 1,1-dioxido)]butylamino-6-methoxy-1,3,4,5-tetrahydrobenz[c,d]-indole hydrochloride.

Examples of heterocyclic radicals which may be mentioned are 1,1-dioxido-3-oxo-2H-1,2-benzisothiazol-2-yl or 4,4-dimethyl-2,6-dioxopiperidin-1-yl.

Of these, 4-(N,N-dipropylamino)-6-methoxy-1,3,4,5-tetrahydrobenz[c,d]indole is particularly preferred.

The tetrahydrobenzindole derivatives are known per se (DE-A 3,346,573; EP-A 153,083; EP-A 162,695) and can be prepared, for example, by reacting 4-amino-6-methoxy1,3,4,5-tetrahydrobenzlc,d]indole and 2-(4-bromobutyl)-1,2-benzisothiazol-3(2H)-one 1,1-dioxide.

Particularly preferred from the group of indolamines are the tryptamine derivatives of the formula

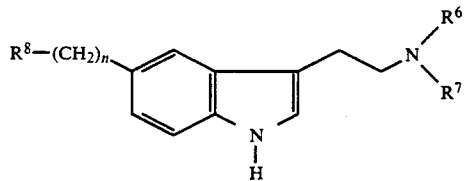

where n represents 1 and

R⁸ represents CONR¹R² or SO₂NR¹R², where R¹ and R² have the abovementioned meanings, and R⁶ and R⁷ are identical or different and denote hydrogen or lower alkyl ($C_1$ to about $C_6$), or n represents the number 0, R⁸ represents CONR¹R², where R¹ and R² have the abovementioned meanings, R⁶ and R⁷ have the abovementioned meanings, or n represents the number 0, R⁸ represents H, OH or OCH₃, R⁶ denotes hydrogen or methyl, and R⁷ represents the radical

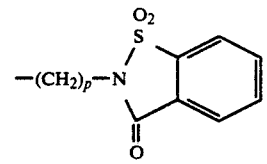

where p represents the values 2, 3, 4 or 5, and/or the salts thereof.

The following active compounds may be mentioned by way of example:

5-carboxamidotryptamine, N,N-dipropyl-5-carboxamidotryptamine, 3-(2-aminoethyl)-1H-indole-5-(N-methyl)acetamide (AH 25 086), 3-(2-dimethylaminoethyl)-1H-indole-5-(N-methyl)methanesulphonamide (GR 43 175), 3-(2-[4-[2-(1,2-benzisothiazole-3(2H)-one 1,1-dioxido)]butyl]amino)ethyl-5-methoxy-1H-indole.

Of these, N,N-dipropyl-5-carboxamidotryptamine and 3-(2-demethylaminoethyl)-1H-indole-5-(N-methyl)-methanesulphonamide are particularly preferred.

The tryptamine derivatives are known per se (Fozard, Trends in Pharmacological Sciences 8, 501 (1987); Scrip's Serotonin Report, PJB Publications (1988); EP-A 236,930; DE-A 3,131,728; DE-A 2,940,687, DE-A 3,320,521) and can be prepared, for example, by reacting 3-(2-bromoethyl)-1H-indole-5-(N-methyl)methanesulphonamide with dimethylamine.

Particularly preferred from the group of aminoalkylbenzodioxanes are the 2-aminomethyl derivatives of the formula

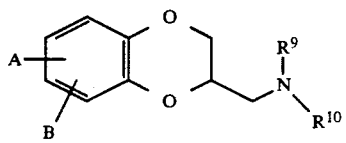

where A and B represent H or together represent —CH=CH—CH=CH— and form a ring,
$R^9$ denotes hydrogen or methyl,
$R^{10}$ represents

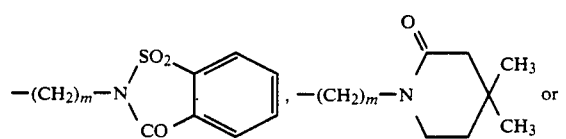

where m represents the numbers 2, 3, 4 or 5, or —$NR^9R^{10}$ represents [1-phenyl-1,3,8-triazaspiro-[4,5]decan-4-on]-8-yl,
and/or the salts thereof.

The following active compounds may be mentioned by way of example:
8-(1,4-benzodioxan-2-yl-methyl)-1-phenyl-1,3,8-triazaspiro[4,5]decan-4-one (INN: spiroxatrine),
8-[4-(1,4-benzodioxan-2-ylmethylamino)butyl]-8-azaspiro[4,5]decane-7,9-dione (MDL 72832),
2-[4-(1,4-benzodioxan-2-ylmethylamino)butyl]-1,2-benzisothiazol-3(2H)-one 1,1-dioxide.

Of these, 2-[4-(1,4-benzodioxan-2-ylmethylamino)-butyl]-1,2-benzisothiazol-3(2H)-one 1,1-dioxide is particularly preferred.

The 2-aminomethyl-benzodioxane derivatives are known per se (EP-A 236,930; Fozard, Trends in Pharmacological Sciences 8, 501 (1987); Scrip's Serotonin Report, PJB Publications (1988); EP 170,213) and can be prepared, for example, by reacting 2-aminomethyl-benzodioxane with 2-(4-bromobutyl)-1,2-benzisothiazol-3(2H)-one 1,1-dioxide.

Particularly preferred from the group of amino-tetralins are the 2-amino derivatives of the formula

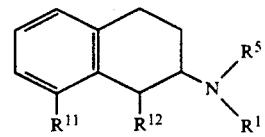

where $R^{12}$ represents H or $CH_3$,
$R^1$ and $R^5$ have the abovementioned meaning, and when $R^{12}$ is H,
and
if $R^5$ is hydrogen or alkyl ($C_1$ to $C_6$),
$R^{11}$ represents OH, $OCH_3$, $NH_2$, $OCOR^1$, $NHCOR^1$ or $NHSO_2CH_3$, where $R^1$ has the abovementioned meaning,
or
if $R^5$ has the abovementioned meaning of —Y—Z, $R^{11}$ represents OH or $OCH_3$,
or
if $R^5$ represents alkyl ($C_1$ to $C_6$),
$R^{11}$ represents —Y—Z or —O—Y—Z, where —Y—Z has the abovementioned meaning,
or
when $R^{11}$ is $CH_3$,
$R^1$ and $R^5$ represent n-propyl,
and/or the salts thereof.

The following active compounds may be mentioned by way of example:
2-(N,N-dipropylamino)-8-hydroxy-1,2,3,4-tetrahydronaphthalene, 2-{4-[2-(1,2-benzisothiazol-3(2H)-one 1,1-dioxido)]butyl}amino-8-methoxy-1,2,3,4-tetrahydronaphthalene.

Of these, 2-(N,N-dipropylamino)-8-hydroxy-1,2,3,4-tetrahydronaphthalene is particularly preferred.

The aminotetralin derivatives are known per se (EP-A 41,488; EP-A 236,930; Arvidsson et al. J. Med. Chem. 30, 2105, 1987) and can be prepared, for example, by reacting 8-methoxy-2-tetralone with dipropylamine under reducing conditions.

Examples from the group of amino-chromans and -thiopyrans which are preferred are the 3-aminochroman and -thiopyran derivatives of the formula

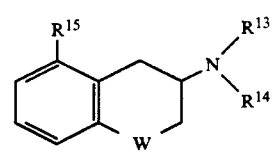

where W represents oxygen or sulphur,
$R^{13}$ and $R^{14}$ have the meaning indicated for $R^1$ and $R^2$, represent aralkyl ($C_7$ to $C_{18}$) or together form a carbocyclic ring ($C_4$ to $C_7$), and
$R^{15}$ represents H, OH or O-alkyl ($C_1$ to $C_6$),
and/or the salts thereof.

The following active compounds may be mentioned by way of example:
3-N,N-dipropylamino-5-hydroxy-thiochroman, 3-N,N-dipropylamino-5-ethoxy-thiochroman, 3-N,N-dipropylamino-5-ethoxychroman.

Of these, 3-N,N-dipropylamino-5-hydroxy-thiochroman is particularly preferred.

The 3-aminochroman and -thiopyran derivatives are known per se (EP-A 222,996) and can be prepared, for example, by reacting 3,4-dihydro-5-methoxy-2H-benzothiopyran-3-amine with propyl iodide.

Particularly preferred from the group of indolylalkyl-piperidines are the 1-[2-(3-indolyl)]ethyl derivatives of the formula

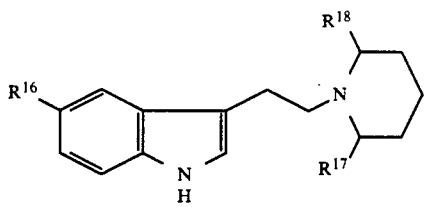

where $R^{16}$ represents H, halogen, methyl, CN or $CONH_2$, and $R^{17}$ and $R^{18}$ are identical or different and represent methyl or ethyl, and/or the salts thereof.

The following active compounds may be mentioned by way of example:
1-[2-(3-indolyl)]-ethyl-2,6-dimethyl-piperidine,
1-{2-[3-(5-carboxamido)indolyl]}ethyl-2,6-dimethyl-piperidine.
Of these,
1-{2-[3-(5-carboxamido)indolyl)]}ethyl-2,6-dimethyl-piperidine is particularly preferred.

The 1-[2-(3-indolyl)]ethyl-piperidine derivatives are known per se (DE-A 3,430,284) and can be prepared, for example, by reacting 1-{2-[3-(5-bromo)indolyl]}ethyl-2,6-demethylpiperidine with sodium cyanide.

Examples from the group of tetrahydropyridines which are preferred are the indolyl-tetrahydropyridine derivatives of the formula

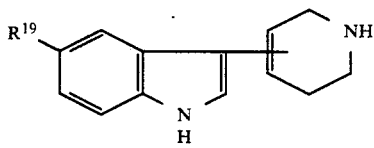

where $R^{19}$ represents H, $OCH_3$, O-ethyl, O-propyl or halogen, and/or the salts thereof.

The following active compounds may be mentioned by way of example:
5-methoxy-3-(1,2,3,6-tetrahydropyridin-4-yl]-1H-indole (RU 24 924),
5-methoxy-3-(1,2,3,6-tetrahydropyridin-5-yl)-1H-indole.
Of these, 5-methoxy-3-(1,2,3,6-tetrahydropyridin-4-yl)-1H-indole is particularly preferred.

The indolyl-tetrahydropyridine derivatives are known per se (EP-A 3,199; SCRIP's Serotonin Report, PJB Publications (1988); Fozard, Trends in Pharmacological Sciences 8, 501 (1987)) and can be prepared, for example, by reacting 4-piperidone with 5-methoxyindole.

The present invention likewise relates to medicaments for the treatment of cerebral apoplexy, which contain one or more active compounds which act as serotonin agonists and have a binding strength of less than 10,000 nmol/l on binding to $5HT_{1A}$ receptors. The medicaments according to the invention generally contain 0.01 to 20% by weight, preferably 0.1 to 10% by weight, of the active compound(s), based on the composition.

The active compounds according to the invention can be converted in a known manner into the customary formulations, such as tablets, coated tablets, pills, granules, aerosols, syrups, emulsions, suspensions and solutions, using inert, non-toxic, pharmaceutically suitable vehicles or solvents.

The formulations are prepared, for example, by extending the active compounds with solvents and/or vehicles, optionally with the use of emulsifiers and/or dispersing agents, and, for example, when using water as a diluent, organic solvents can optionally be used as auxiliary solvents.

Examples of auxiliaries which may be mentioned are: water, non-toxic organic solvents, such as paraffins (for example petroleum fractions), vegetable oils (for example groundnut oil/sesame oil), alcohols (for example ethyl alcohol and glycerol) and glycols (for example propylene glycol and polyethylene glycol), solid vehicles, such as, for example, natural rock powders (for example kaolins, aluminas, talc and chalk), synthetic rock powders (for example highly disperse silica and silicates) and sugars (for example sucrose, lactose and glucose), emulsifiers (for example polyoxyethylene fatty acid esters, polyoxyethylene fatty alcohol ethers, alkylsulphonates and arylsulphonates), dispersing agents (for example lignin, sulphite waste liquors, methylcellulose, starch and polyvinylpyrrolidone) and lubricants (for example magnesium stearate, talc, stearic acid and sodium lauryl sulphate).

Administration is effected in the customary manner, preferably orally or parenterally, in particular perlingually or intravenously. In the case of oral administration, tablets can, of course, also contain, in addition to the vehicles mentioned, additives such as sodium citrate, calcium carbonate and dicalcium phosphate, together with various additional substances, such as starch, preferably potato starch, gelatine and the like. Furthermore, lubricants such as magnesium stearate, sodium lauryl sulphate and talc can also be used when making tablets. In the case of aqueous suspensions, the active compounds can be mixed with various flavor-improving agents or colorants in addition to the abovementioned auxiliaries.

In the case of parenteral administration, solutions of the active compounds, employing suitable liquid vehicles, can be used.

In general, it has proved advantageous, in the case of intravenous administration, to administer amounts of about 0.001 to 1 mg/kg, preferably about 0.01 to 0.5 mg/kg, body weight to achieve effective results, and in the case of oral administration, the dosage is about 0.01 to 20 mg/kg, preferably 0.1 to 10 mg/kg, body weight.

Nevertheless, it can at times be necessary to deviate from the amounts mentioned, and in particular to do so as a function of the body weight or of the nature of the administration method, but also because of the individual behavior towards the medicament, or the nature of the formulation of the medicament and the time or interval over which the administration takes place. Thus it can suffice in some cases to manage with less than the above-mentioned minimum amount, whilst in other cases the upper limit mentioned must be exceeded. Where relatively large amounts are administered, it can be advisable to divide these into several individual administrations over the course of the day.

The mode of action of the active compounds according to the invention for the preventive and subsequent treatment of cerebral apoplexy can be indentified using the method of focal cerebral ischaemia in the rat as stroke model (Middle Cerebral Artery Occlusion (MCA)). Reference: A. Tamura et al.; J. Cerebral Blood Flow and Metab. 1, 53–60, 1981.

The treatment of cerebral apoplexy with the active compounds according to the invention represents a new and surprising treatment principle.

EXAMPLES

Test Model

1. Occlusion of the middle cerebral artery in the rat

Under anaesthesia ($N_2O$/halothane) a skin incision is made centrally between the eye and ear and, by blunt dissection of the underlying areas of muscle, an access to the skull is created in the region of the foramen ovale. The cranial bone is removed about 1 mm rostrodorsal from this opening, the underlying meninges are opened, and the middle cerebral artery is occluded by electrocoagulation. The musculature is then returned to its original position, and the incised area of skin is sewn together again. The animals are returned to their home cages. An infarct develops during the following few hours in the region of flow of the artery, and its extent is quantified histologically.

2. Quantification of the infarct size 48 hours after the occlusion of the vessel, the brains are fixed by perfusion with phosphate-buffered (pH 7.4) formalin solution, removed from the skull, embedded in paraplast and cut up into thin sections (8 $\mu$m). The brain sections are stained with cresyl violet to distinguish between intact and damaged tissue. On each of about 15 sections 0.5 mm apart the areas for the entire hemisphere, the entire cortex, the entire striatum and the corresponding damaged areas are determined by planimetry using an image-analysis system. The infarct volume is then determined from the areas of consecutive sections and the relevant spacings, specifically for the cortex, striatum and total volumes separately.

3. Treatment with pharmaceutical substances

The animals were generally treated with pharmaceutical substance 30 minutes before the occlusion of the vessel. The substances were taken up in physiological saline and administered intraperitoneally in a volume of 1 ml/kg. The dosage was between 1 and 30 mg/kg of body weight. In another series, ipsapirone (30 mg/kg) was administered intraperitoneally 1 hour after the occlusion of the vessel. The results of the investigations are shown in the table by way of example. The infarct volume is significantly reduced in the presence of each of the pharmaceutical substances.

The following active compounds were investigated using this test:

| Example | Active compound | Infarct volume in the cortex without treatment | Infarct volume in the cortex with treatment |
|---|---|---|---|
| 1 | 8-OH-DPAT (1 mg/kg) | 61.7 +/− 10.4 | 40.7 +/− 15.5* |
| 2 | Bay R 1531 (1 mg/kg) | 61.7 +/− 10.4 | 24.0 +/− 18.6*** |
| 3 | Buspirone (10 mg/kg) | 66.1 +/− 12.9 | 38.5 +/− 14.4** |
| 4 | Gepirone (10 mg/kg) | 77.2 +/− 32.3 | 39.6 +/− 31.4* |
| 5 | Ipsapirone (10 mg/kg) | 70.0 +/− 21.4 | 40.8 +/− 23.5* |
| 6 | Ipsapirone (30 mg/kg) | 36.5 +/− 12.2 | 13.7 +/− 5.4*** |
| 7 | Ipsapirone (30 mg/kg; 1 hour after MCA occlusion) | 66.1 +/− 12.9 | 31.5 +/− 20.9** |

*$p < 0.05$
**$p < 0.01$
***$p < 0.001$
(H test or U test)

It is understood that the specification and examples are illustrative but not limitative of the present invention and that other embodiments within the spirit and scope of the invention will suggest themselves to those skilled in the art.

We claim:

1. A method of treating cerebral apoplexy in a patient in need thereof which comprises administering to said patient an amount effective therefor of a serotonin agonist which has a binding strength of less than 10,000 nmol/l on binding to $5HT_{1A}$ receptors, the serotonin agonist being selected from the group consisting of an aminoalkyl-benzadioxane and an aminotetralin.

2. The method according to claim 1, wherein the serotonin agonist has 1,000 nmol/l.

3. The method according to claim 1, wherein the serotonin agonist has a binding strength in the range 0.1 to 100 nmol/l.

4. The method according to claim 1, wherein the serotonin agonist is an aminotetralin.

* * * * *